United States Patent [19]

Courbat et al.

[11] 4,153,788
[45] May 8, 1979

[54] PROCESS OF PREPARING MONO-O-β-HYDROXYETHYL-7 RUTOSIDE

[75] Inventors: Pierre Courbat, Nyon; Alban Albert, Avuilly, both of Switzerland

[73] Assignee: ZYMA S.A., Nyon, Switzerland

[21] Appl. No.: 775,201

[22] Filed: Mar. 7, 1977

Related U.S. Application Data

[63] Continuation-in-part of Ser. No. 561,434, Mar. 24, 1975, abandoned.

[30] Foreign Application Priority Data

Apr. 9, 1974 [CH] Switzerland .......................... 4959/74

[51] Int. Cl.² ........................................... C07H 23/00
[52] U.S. Cl. ...................................... 536/8; 424/180; 536/121
[58] Field of Search ................................... 536/8, 120

[56] References Cited

U.S. PATENT DOCUMENTS

| | | | |
|---|---|---|---|
| 2,450,555 | 10/1948 | Koones | 536/8 |
| 3,305,535 | 2/1967 | Merten et al. | 536/120 |
| 3,420,815 | 1/1969 | Courbat | 536/8 |

*Primary Examiner*—Johnnie R. Brown
*Attorney, Agent, or Firm*—Stevens, Davis, Miller & Mosher

[57] ABSTRACT

A process is provided for preparing mono-O-β-hydroxyethyl-7-rutoside of the formula:

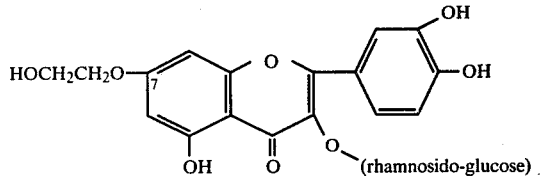

which comprises contacting rutoside of the formula:

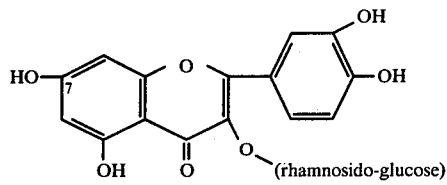

in a solvent which is an at least partially aqueous medium with a boric acid alkali salt in an amount substantially not exceeding the amount necessary to form a boron complex of formula:

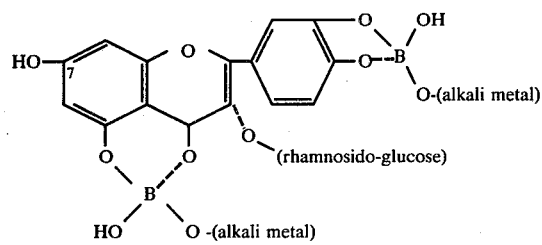

reacting said boron complex with ethylene oxide to form a hydroxyethoxy compound of the formula

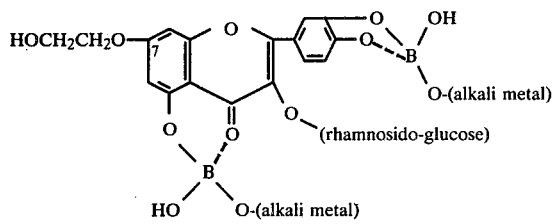

and treating said hydroxyethoxy compound in an at least partially aqueous acid medium, whereby there is produced said mono-O-β-hydroxyethyl-7-rutoside.

7 Claims, No Drawings

PROCESS OF PREPARING MONO-O-β-HYDROXYETHYL-7 RUTOSIDE

This application is a continuation-in-part of our copending application Ser. No. 561,434 filed Mar. 24, 1975, now abandoned.

SUMMARY OF THE INVENTION a process is provided for preparing mono-7-HER (mono-O-β-hydroxyethyl-7-rutoside) which has the formula:

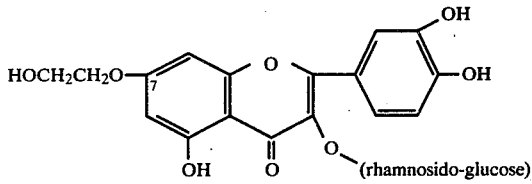

The process of the invention comprises contacting rutoside of the formula:

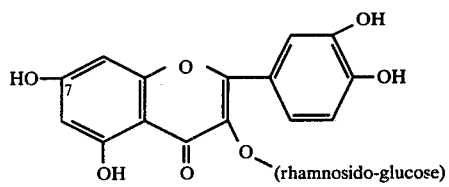

in a solvent which is an at least partially aqueous medium with a boric acid alkali salt in an amount substantially not exceeding the amount necessary to form a boron complex of formula:

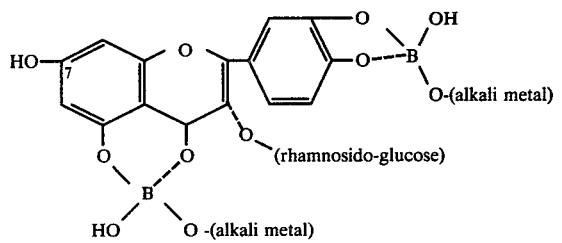

Sodium may be mentioned as the alkali metal; the aforesaid boron complex is then reacted with ethylene oxide to form a hydroxyethoxy compound of the formula:

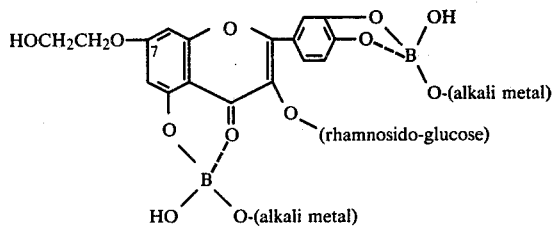

This hydroxyethoxy compound is then treated in an at least partially aqueous acid medium to yield the desired mono-7-HER.

DETAILED DESCRIPTION OF THE INVENTION

The known hydroxyethylation of rutoside for example by means of ethylene chlorhydrin and employing stoichiometric quantities of alkali, or by means of a great excess of ethylene oxide in the presence of alkali always leads to a more or less complex mixture of O-β-hydroxyethyl derivatives of rutoside from which one or other of the components cannot be isolated on an industrial scale.

Only ethylene oxide as hydroxyethylation agent enables production of the 7-mono-etherified derivative of rutoside in practically pure state according to a known process teaching the use of hydro-alcoholic solvents or water-dioxane mixtures to slow the speed of hydroxyethylation. In this known process, the duration of the reaction leads to the formation of different hydroxyethyl derivatives which successively pass from the mono-derivatives to di- and tri-derivatives and even tetra-derivatives. It was thus necessary to permanently control the reaction and to be able to interrupt it after the formation of mono-7-HER, this being a delicate operation. The process according to the invention does not have this drawback, as the reaction cannot continue beyond mono-etherification and because of this the yield obtained is superior.

According to the known process, the temperature of the reaction was relatively high, namely above 50° C. and preferably between 80 and 90° C., whereas in the process according to the present invention, the reaction temperature preferably remains below 50° C., and can be kept between 30° and 40° C.

According to the process of the invention, the consumption of ethylene oxide is reduced and it is used in safer conditions.

According to the known process, several successive crystallisations are required. According to the new process, the quantitative hydroxyethylation of rutoside is controlled and there is formed, beside the mono-7-HER, only traces of di-Oβ-hydroxyethyl-5,7 rutoside and tri-0-hydroxyethyl-7,3',4' rutoside, the two latter substances being soluble in water and hence easy to eliminate by a single crystallisation which leaves the chromatographically pure mono-7-HER.

The soluble rutoside complex used in the process of the invention may be obtained by reacting preferably practically equimolar quantities of borax. The reaction solvent may be aqueous or partially aqueous. The complex may be directly prepared before hydroxyethylation and need not necessarily be isolated from the reaction medium before proceeding to the hydroxyethylation. For example, in water, formation of the borax-rutoside complex may be controlled by visible spectrography (rutoside absorbs at 359 nm and the rutoside-borax complex at 379 nm) or by ultraviolet spectrography (rutoside absorbs at 255 nm with a shoulder at 260 nm whereas the rutoside-borax complex absorbs at 268 nm with a shoulder at 330 nm). In partially aqueous or polar organic media, such as in mixtures of water with methanol or ethanol, the rutoside-boric acid complex may for example be detected by ultraviolet-visible spectrography.

Hydroxyethylation is carried out directly on the complex by means of a measured quantity of ethylene oxide, preferably 2.5 moles or more per mole of rutoside; it is favourized in aqueous media by a slight excess of borax, and in organic polar media by a weak base such as sodium acetate.

The process according to the invention may be carried out in the laboratory in an autoclave and industrially in a reactor, for example of the Grignard type able to be hermetically closed.

The etherification reaction takes place at a relatively low temperature, below 50° C., preferably between 30° and 40° C. At higher temperatures, there is a risk of decomposition of the complex, which would lead to a non-sought mixture of 0-β-hydroxyethyl derivatives of rutoside. The reaction can take place in relatively concentrated solutions of the complex, for example above 30% by weight.

Progression of the reaction can be controlled chromatographically on a thin film of cellulose by means of a butanol-n-methanol-water mixture (10:1:3 by volume). The reaction is finished upon the quantitative disappearance of rutoside. Then, while cooling to ambient temperature, the residual ethylene oxide is removed, for example by passing an inert gas such as nitrogen into the reactor; this drives off the residual ehtylene oxide which can be taken up by bubbling it in an aqueous solution of 6N hydrochloric acid. The solution is then acidified, preferably to a pH comprised between 1 and 3, for example by means of a concentrated acid solution, preferably a mineral acid such as 20% hydrochloric acid. This acidity destroys the previously formed complex. Isolation of the desired substance may for example be obtained as follows: in water, the mono-7-HER derivative precipitates whereas in partially aqueous and organic polar solvents, the reaction solvent is replaced by water and the pH of the solution is controlled to be brought to between 1 and 3, which enables precipitation of the mono-7-HER.

At this stage, the yield of practically pure mono-7-HER in purely aqueous reaction media is of the order of 97-98%, i.e. far superior to the known process. Moreover, it is possible to easily remove the impurities which are soluble in water.

A simple recrystallisation in water leads to chromatgraphically pure mono-7-HER.

The purity of the produce can be controlled chromatgraphically on a thin layer of polyamide by using as solvent a butanol-n-methanol-water mixture (10:1:3 by volume) or by chromatographing its aglucon (obtained by acid hydrolysis) on S+S 2034 bmgl paper by means of formic acid-water solvent (7:3 by volume) according to the descending technique.

The produce is also confirmed by mass spectrography in the presence of various reactants such as sodium acetate, sodium methylate, sodium acetate/boric acid mixture, aluminium chloride with or without hydrochloric acid.

The produce considered, mono-7-HER, notably has the following pharmacological properties: normalization of the capillary permeability, increase of the capillary resistance, action on the metabolism of the conjunctive tissue, action on the energetic metabolism of the vascular wall and an anti-inflammatory action. It has multiple medical applications: the treatment of circulatory troubles in particular troubles in the veins and capillaries, and of certain troubles of the metabolism of the conjunctive tissues. It is possible to incorporate it in various pharmaceutical presentations, in determined and fixed proportions.

EXAMPLE 209 g i.e. 0.55 mole of borax Na₂B₄O₇.10 H₂O is dissolved in 1150 ml of distilled or demineralised water, and 310 g i.e. 0.51 mole of rutoside is added and progressively passes into solution to form the rutoside-borax complex. The solution is stirred and held at 40° C. in an autoclave. By pumping out ambient air, the autoclave is placed under slight vacuum, and 62.5 ml i.e. 56 g or 1.275 mole of ethylene oxide is added by injection with nitrogen under slight pressure, and normal pressure is re-established with nitrogen. Stirring is continued at the temperature of 40° C. during 24 hours, the time required for entire disappearance of the rutoside. Heating is stopped, and a stream of nitrogen passed during 2 hours to drive off the residual ethylene oxide which is trapped by passing the stream of gas through a washing bottle containing 1 liter of 6N hydrochloric acid.

After transfer to a 2-liter erlenmeyer flask the reaction solution is brought to pH 2.0 by adding 180 ml of 20% hydrochloric acid (5.5N HCl): the precipitation of mono-7-HER begins during acidification. The solution is left at 4° C. overnight then the precipitate is separated by filtration, and washed with cold water.

The dried substance weighs about 320 g, i.e. a yield of 97%.

What we claim is:

1. A process for preparing mono-O-β-hydroxyethyl rutoside of the formula:

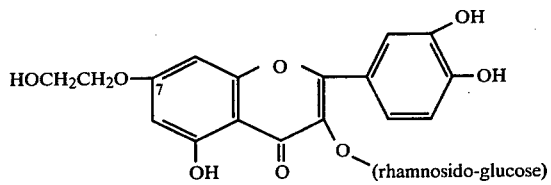

which comprises contacting rutoside of the formula:

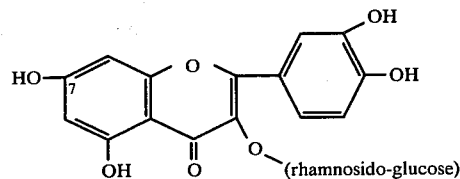

in a solvent which is an at least partially aqueous medium with a boric acid alkali salt in an amount substantially not exceeding the amount necessary to form a boron complex of formula:

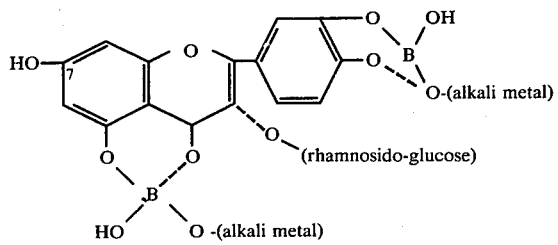

reacting said boron complex with ethylene oxide to form a hydroxyethoxy compound of the formula

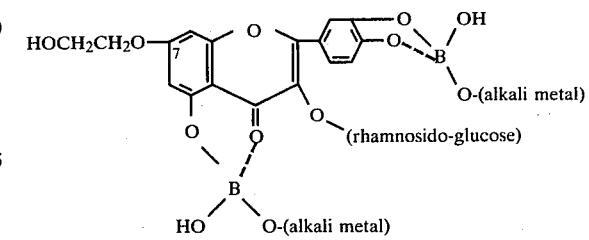

and treating said hydroxyethoxy compound in an at least partially aqueous acid medium, whereby there is produced said mono-O-β-hydroxyethyl-7-rutoside.

2. A process of claim 1 wherein said alkali metal is sodium.

3. The process of claim 2, wherein the solvent is water.

4. The process of claim 2, wherein the solvent is a mixture of water and a lower aliphatic alcohol.

5. The process of claim 2, wherein said boric acid salt is borax of formula $Na_2B_4O_7.10.H_2O$ used in an amount substantially equimolar to the amount of rutoside.

6. The process of claim 2, wherein the reaction with ethylene oxide is carried out in the presence of sodium acetate as a catalyst.

7. The process of claim 2, wherein the reaction with ethylene oxide is made at a temperature between 30° and 50° C.

* * * * *